United States Patent [19]
Willard

[11] Patent Number: 5,746,749
[45] Date of Patent: May 5, 1998

[54] RECTOVAGINAL SURGICAL REPAIR INSTRUMENT

[76] Inventor: Cindylee Willard, 615 Justis St., Mountain Home, Ark. 72653

[21] Appl. No.: 625,683

[22] Filed: Apr. 26, 1995

Related U.S. Application Data

[63] Continuation-in-part of Ser. No. 181,820, Jan. 18, 1994, abandoned.

[51] Int. Cl.$^6$ ................................................ A61B 17/42
[52] U.S. Cl. .................................... 606/119; 606/191
[58] Field of Search .............................. 128/778, 830, 128/841, 885, 887; 604/11–15; 606/1, 119, 191, 197

[56] References Cited

U.S. PATENT DOCUMENTS

| | | | |
|---|---|---|---|
| 719,487 | 2/1903 | Minor | 606/191 |
| 1,008,017 | 11/1911 | Crittenden | 604/104 |
| 2,056,678 | 10/1936 | Kolling | 606/197 |
| 2,290,571 | 7/1942 | Peyton | 606/197 |
| 3,132,645 | 5/1964 | Gasper | 128/3 |
| 4,106,489 | 8/1978 | Martin | 606/191 |
| 5,007,895 | 4/1991 | Burnett | 604/11 |
| 5,290,294 | 3/1994 | Cox et al. | 128/7 |

OTHER PUBLICATIONS

V. Mueller & Co. Chicago—Surgical Instruments Catalog. Rectal Instruments pp. 490.

*Primary Examiner*—Glenn K. Dawson
*Attorney, Agent, or Firm*—Thad G. Long

[57] ABSTRACT

A rectovaginal surgical instrument for the repair of rectovaginal tears, incisions and fistulas, especially those associated with childbirth. The instrument includes an elongated generally cylindrically shaped member, one end being continuously curved toward a tip and the other end having a flange and optionally wing guides, curved, or post guides, for retaining and/or guiding forceps or other surgical instruments.

11 Claims, 3 Drawing Sheets

RECTOVAGINAL SURGICAL REPAIR INSTRUMENT

This application is a continuation-in-part of U.S. Ser. No. 08/181,820, filed Jan. 18, 1994 and entitled "Rectovaginal Surgical Repair Instrument", which is co-pending and is hereby abandoned.

FIELD OF INVENTION

The present invention relates to a surgical device to aid in the repair of rectovaginal tears, incisions and fistulas, especially those which occur in connection with childbirth and require suturing at the conclusion of the childbirth process.

BACKGROUND OF THE INVENTION

Despite the many advances in modern medical and surgical procedures, there are some procedures which remain relatively unchanged.

In childbirth, tissue in and around the vagina and the vaginal opening quite often is torn or is surgically incised in an episiotomy during or in anticipation of parturition. Such tears or incisions must be surgically repaired by suturing after delivery. During the period before the repair has been accomplished, the mother may be in considerable discomfort and may be bleeding heavily. There is a need to accomplish the suturing as quickly as possible to relieve or minimize the discomfort and decrease the amount of blood loss.

The difficulty in making surgical repairs of episiotomies or third or fourth degree lacerations in the rectovaginal area is that suturing must be done on muscle and other tissue in a body area where there is restricted access and often bleeding and other body fluids. As a consequence, physicians and other healthcare attendants involved in such repair procedures most frequently insert one of their own fingers into the patient's rectum to maintain separation of the upper and lower portions of the rectum, and to provide appropriate firmness.

The use of the human finger in such manner has many disadvantages. One important problem is that the physician or healthcare attendant must sew with only one free hand available for that purpose, the other hand being used to provide the support for the tissue being sutured. Second, the process is slow in that the suturing must be constantly checked to insure that it is not too deep, that there are no gaps, and that the suturing is otherwise proceeding properly, all of which prolongs the discomfort of the patient and potentially increases blood loss. There is also an increased risk of infection to both the healthcare provider and the patient. If the nurse is asked to place a finger in the rectum, the procedure goes somewhat faster, but the risk of infection remains in the event of the needle pricking the finger.

There is no surgical instrument available to physicians or healthcare attendants to provide these functions in connection with such suturing. On occasion, it is said that test tubes have been used, but clearly this is not a proper use for test tubes, which can break, causing severe cuts, and which can potentially slide wholly inside the rectum, necessitating retrieval.

A search of medical literature, patents and surgical instrument catalogs does not reveal any instrument available to provide support to aid in the suturing in the context considered here. Clearly, there is a need for an instrument which provides the necessary support, not only in the case of vaginal tear s and episiotomies, but also in the case of colostomies and other operations in the vicinity of the vagina and anus. The Peters U.S. Pat. No. No. 4,964,417, dated Oct. 23, 1990, reveals a wound closure aid designed to cover, protect and retain internal organs in the course of a wound repair, by being tucked under adjacent tissue and then withdrawn just before the wound is completely closed. It is designed for a different purpose and, being of a generally two-dimensional curved configuration, would not at all be suitable for suturing an episiotomy. In addition, British patent 638,892, published Jun. 14, 1950, reveals a device for insertion of sutures prior to delivery in the area where the incision is expected to be made, so that the incision can be closed after delivery imply by "lacing up" the sutures which have been pre-inserted. The British patent does not appear to have been significantly utilized, if at all, possibly because of dangers to the child —and possibly to the mother —arising from delivery across in-place sutures which could pose both an impediment to delivery and possible dangers. In any case, the instrument would be useless as an aid to suturing after an episiotomy not involving previously inserted sutures. There are rectal dilators designed to deal with bowel prolapse and to inject medication into the rectum, such as Lott U.S. Pat. No. 988,120, issued Mar. 28, 1911 and British patent 233,903 issued May 21, 1925. There are also vaginal dilators such as is exemplified by the Waters U.S. Pat. No. 2,763,265 issued Sep. 18, 1956. However, the irregular shape of these instruments and the holes in one of them render these instruments unsuitable as aids in suturing. Nor has anyone, to the inventor's knowledge, ever suggested that they be employed as an aid for suturing.

The present invention in one preferred embodiment is a smooth rigid cylinder, sized to fit snugly, with a continuous curved tip at one extremity thereof and with a rim-type flange devise at the opposing extremity thereof which also optimally allows some manipulation, if useful, of the inserted cylindrical portion of the invention. To enhance the usefulness of the inventions, rigid "wing" devices may be incorporated on or near and rigidly attached to the flange or stop which can help, when engaged with forceps which are used to hold the sphincter in place for later suturing and to retain the invention in its proper place during suturing, thus freeing the hands of physicians and healthcare attendants to do their work with a minimum of obstructions. Although this invention is relatively simple and uncomplicated, it serves a function and satisfies a need for which there is no other surgical instrument. The need is clear, and it is significant that the thousands of obstetricians, gynecologists, physicians, and midwives throughout the world who regularly deliver babies have thus far not, to the applicant's knowledge, produced or used such a devise, nor have the medical supply industries which are constantly seeking new and improved surgical products.

DETAILED DESCRIPTION OF THE DRAWINGS

Figure 1:
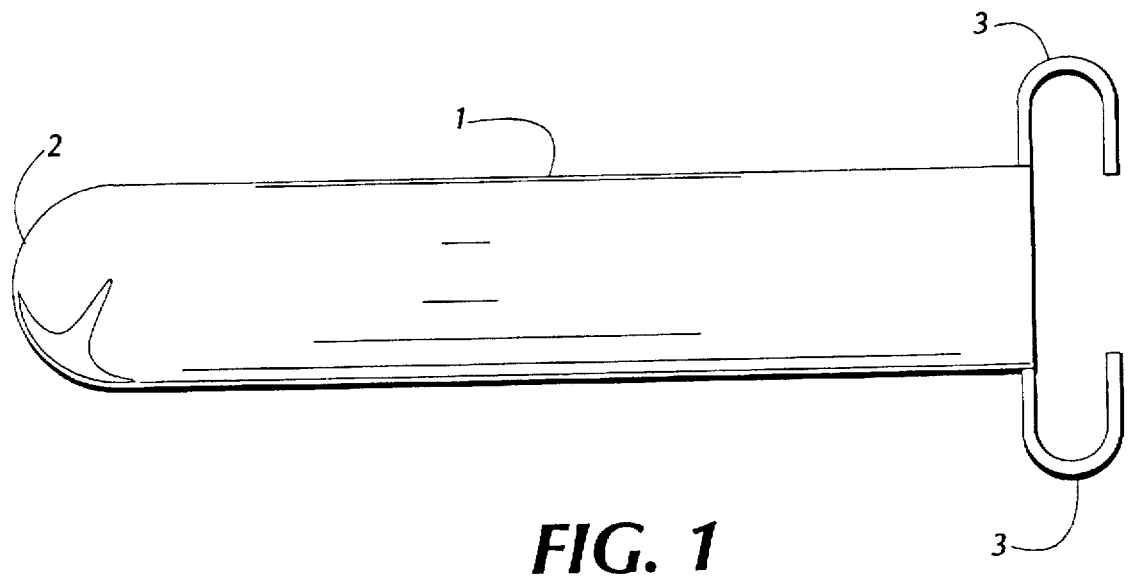
FIG. 1 is a drawing of one preferred embodiment of the invention having a pair of inwardly curved wing devices 3.

Referring to FIG. 1, an elongated cylindrical member 1 has a rounded or blunted end 2, which is the end designed for insertion into the patient. "Wing" devices 3 are affixed at the opposite end therefrom in which to engage the handles of forceps in a manner to be described below. Wings serve also to immobilize substantially the instrument after insertion, to prevent migration further into or regression from the patient, when the forceps at one end are engaged with the wings and at the other end are grasping muscle tissue, as detailed below. While the wing devices 3 preferably curved inwardly but without touching, the wing devices 3 could be like a pair of posts not curving inwardly, in which case they would function as guides and stops for the forceps but would not actually engage the forceps to the extent of inwardly curving wings. (See discussion in connection with FIG. 5 below.) On the other hand, the wing devices could curve inwardly and meet, or even form a continuous loop, encircling the forceps inserted therein.

Figure 2:
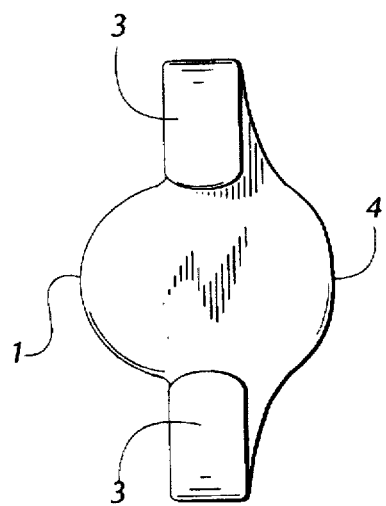
FIG. 2 is a drawing showing the invention of FIG. 1 viewed along the axis of the cylindrical portion of the invention.

FIG. 2 is a view of the invention shown in FIG. 1, shown from the wings-end thereof and looking along the axis of the elongated cylindrical member. An end of the elongated cylindrical member 1 is shown, as well as the wing devices 3. In addition, in this embodiment there is shown a flange 4 which serves as an enhancement of the "stop" function of the wing devices 3. It should be noted that the flange 4 appears on only one side of the wing devices 3. The reason for limiting the flange 4 to one side only is that a flange extending all the way around would interfere with the suturing and medical care being administered by the healthcare professional, as will be explained later in this specification.

Figure 3:
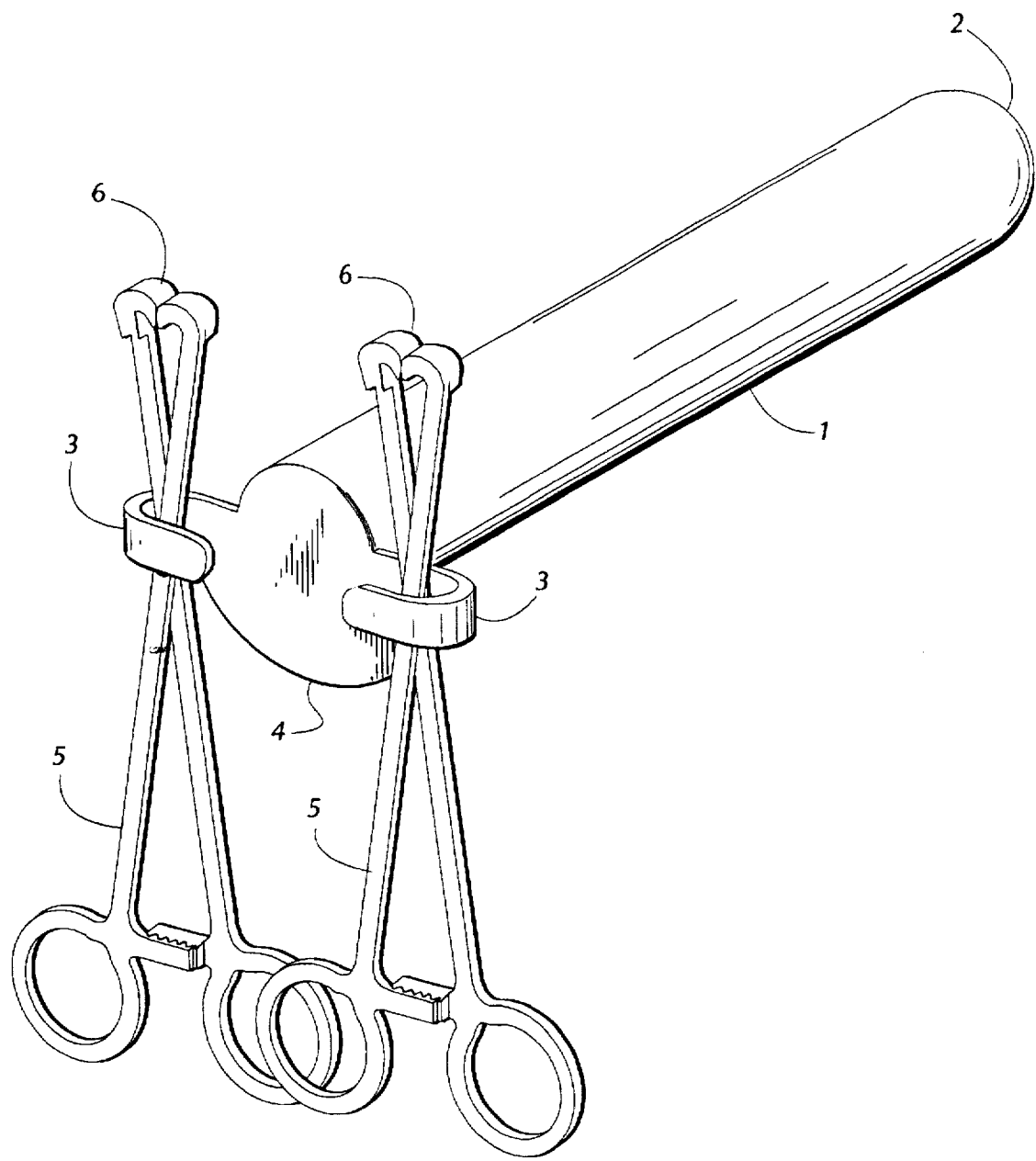
FIG. 3 is a drawing showing the invention of FIG. 1 with forceps engaged with inwardly curved wing devices 3.

FIG. 3 shows a pair of forceps 5 engaged with the wing devices 3. In an episiotomy repair procedure, the extremities 6 of the forceps 5 would be grasping sphincter muscle tissue having previously been severed, to hold such tissue together for suturing after parturition. By engaging the forceps 5 with the wing devices 3, the forceps 5 perform the dual function of retaining in place the member 1 of the invention and at the same time positioning the sphincter muscles for suturing.

Figure 4:
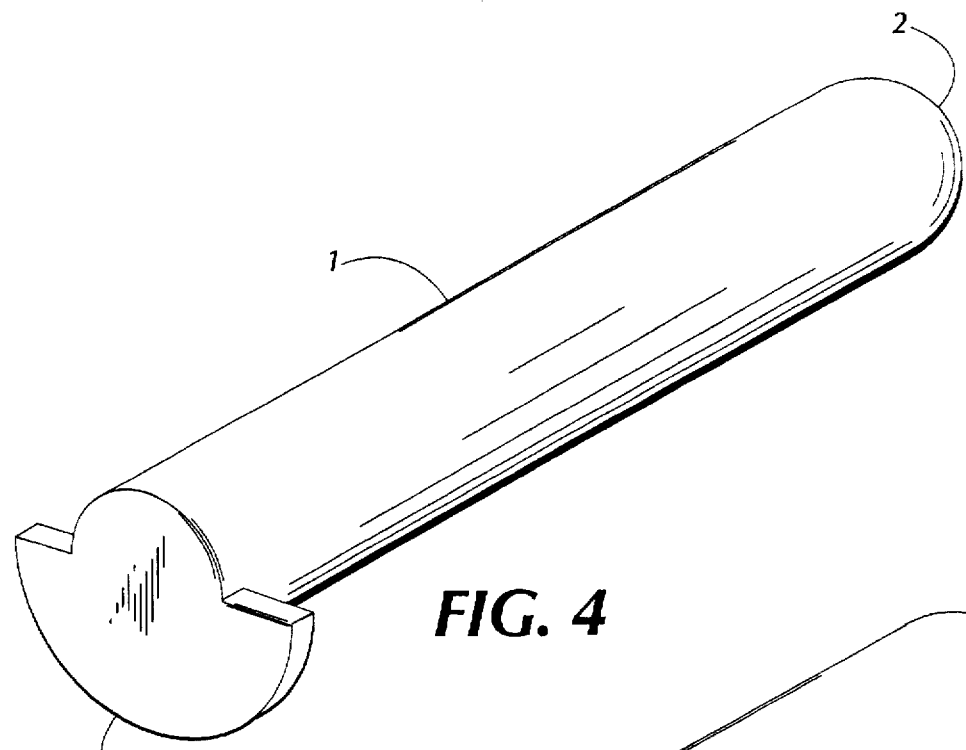
FIG. 4 is a drawing of an alternative preferred embodiment of the invention wherein there is a partial flange but no wing devices.

FIG. 4 shows an elongated cylindrical member 1 with rounded or blunted extremity 2 and a partial flange 4 attached to the end opposite said extremity. Extremity 2 is inserted into the patient, and flange 4 serves both as a stop and as a means for facilitating retraction of the instrument from the patient. To avoid obstructing or impeding the suturing procedures, the flange should not normally extend substantially farther than 180° about the circumference of the elongated cylindrical member. For certain limited situations, it is possible that a flange extending farther would not be disadvantageous; but for general use it would be desirable that there be no flange across a significant part of the circumference so that the flanged portion can be positioned in a direction to avoid obstruction of work while serving as an effective stop. It is to be noted that FIG. 4 shows the invention without the wing devices which are a part of the invention as shown and discussed in connection with FIGS. 1–3. Some physicians and healthcare professionals may prefer to work with the invention without wing devices because of a preference for having forceps free of any restraint on their mobility, and the embodiment of FIG. 4 is designed for use in that event.

Figure 5:
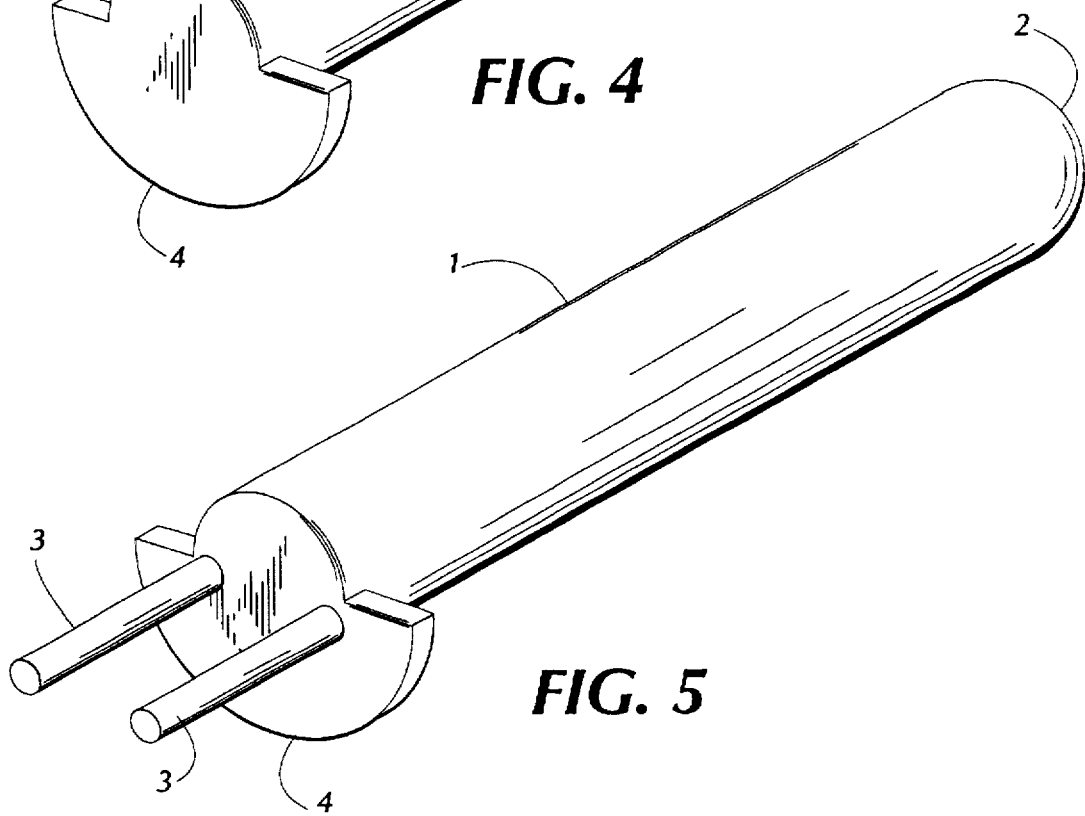
FIG. 5 is a rim-type drawing of an alternative preferred embodiment of the invention wherein the wing devices are posts.

FIG. 5 shows an alternative embodiment of the invention, similar to FIG. 1–3, except that the wing devices 3 in FIG. 5 are posts which serve primarily as lateral guides. This configuration allows for relatively greater maneuverability than the inwardly curving wings and may be considered desirable where one wishes to have forceps engaged sufficiently to retain the invention in place but simultaneously free enough to "escape" instantaneously without the concern of disengaging from the inwardly curving wing devices shown in FIGS. 1–3 above. Obviously, there could be a row of post wings on opposing sides or there could be post wings of a rectangular "wall" configuration, and nothing herein is intended to limit the invention to any particular configuration.

Figure 6:
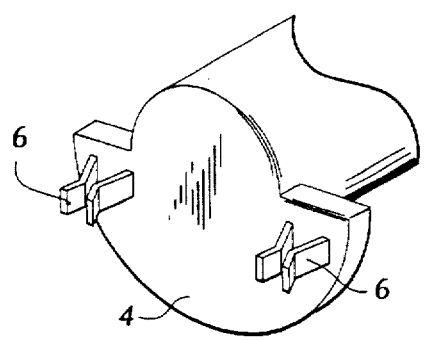
FIG. 6 is a drawing of still another preferred embodiment of the invention showing a clip mechanism attached to a flange.

FIG. 6 shows the flanged end of still another an alternative preferred embodiment of the invention. The opposing end not shown is substantially the same as the corresponding parts of the invention as shown in FIGS. 1, 3, 4 and 5 above. However, clip or fastener means 6 have been provided to secure forceps (not shown) with even greater security than that represented by the wing devices of FIGS. 1–3, and 5, above. This configuration of the invention would be used when the highest degree of security and stability is desired, as opposed to the loose and slightly more maneuverable configuration represented by the wing devices of FIGS. 1–3. The clip or fastener means 6 can be of any design which will secure and hold the forceps tightly, such as a hasp or pinch-type clip or any other clip or fastener design.

The subject invention can be made of any smooth, rigid, non-toxic material, but the material should preferably be nonmagnetic, to avoid attraction to surgical instruments during suturing procedures, and nonbreakable under normal noncompressive use. The subject invention should also preferably be impervious so that germs, bacteria and viruses do not become imbedded in the pores, especially if the instrument might possibly be reused. Normally, the instrument can be reused if it can be effectively and efficiently sterilized after use, which generally will require that it be impervious and able to withstand heat and/or chemical and/or ultrasound or other sterilization substances and procedures. Non-magnetic surgical stainless steel or a tough acrylic or plastic will be suitable. The instrument can optionally be hollow or solid. It will often be useful if the instrument weighs at least several ounces, since a greater mass tends to prevent its being dislodged or ejected after insertion as a result of natural muscle contractions in the rectum.

The diameter of the elongated member 1, as shown in each of the respective drawings, at its widest point should normally be in the range of 1 cm to 4 cm, generally approximately 2 cm. It would normally be unnecessary for said elongated member 1 to exceed 15 cm in length and it will normally need to be longer than 3 cm to be effective, with an optimal length being approximately 8 to 10 cm. The partial flange 4 in aforesaid drawings normally should extent out at least 0.5 cm from the circumference of elongated member 1. The wing devices 3 should not need to exceed 8 cm from outer tip to outer tip nor should they normally be shorter from outer tip to outer tip than the diameter of said elongated member 1 at its widest point. The wing devices may touch each other as they curve inwardly, or even form a continuous loop, although the disengagement of the forceps from the wing devices is facilitated when there is some open space between the two wing devices.

What is claimed is:

1. A rectovaginal surgical repair instrument comprising:
   (a) a smooth, rigid elongated cylindrical member having a first end and a second end and a longitudinal axis, said cylindrical member having a length in the range of 3 cm to 15 cm and a diameter such that at a widest point of said cylindrical member said diameter is in the range of 1 cm to 4 cm; and (b) at least one rigid, open looped wing device rigidly attached to and extending outwardly from said first end, said looped wing device further curving back inwardly to a point such that the perpendicular distance between said point and said longitudinal axis is less than the radius of said cylindrical member.

2. A rectovaginal surgical repair instrument as described in claim 1 wherein said cylindrical member has a continuously curved shape at said second end.

3. A rectovaginal surgical repair instrument as described in claim 1 wherein, near said first end having said wing device, there is a rim-type flange extending about a part of the circumference of said cylindrical member outward therefrom at least 0.5 cm.

4. A rectovaginal surgical repair instrument comprising:

(a) a smooth, rigid, elongated cylindrical member having a first end and a second end and a longitudinal axis, said elongated cylindrical member having a length in a range of 3 cm to 15 cm and a diameter range at its widest point of 1 cm to 4 cm; and (b) two generally opposing rigid, wing devices rigidly attached to and extending outwardly from said first end of said elongated cylindrical member and then curving back inwardly to respective points such that the perpendicular distance between each of said points and said longitudinal axis is less than the radius of said cylindrical member.

5. A rectovaginal surgical repair instrument as described in claim 4 wherein said cylindrical member has a continuously curved shape at said second end.

6. A rectovaginal surgical repair instrument as described in claim 4 wherein, near said first end having said wing device, there is a rim-type flange extending about a part of the circumference of said cylindrical member outward therefrom at least 0.5 cm.

7. A rectovaginal surgical repair instrument comprising:

(a) a smooth, rigid, elongated cylindrical member having a first end and a second end, said elongated cylindrical member having a length in a range of 3 cm to 15 cm and a diameter range at its widest point of 1 cm to 4 cm; and (b) at least one rigid, closed looped wing device rigidly attached to and extending outwardly from said first end of said elongated cylindrical member and having curvilinear length greater than the diameter of said cylindrical member.

8. A rectovaginal surgical repair instrument as described in claim 7 wherein said cylindrical member has a continuously curved shape at said second end.

9. A rectovaginal surgical repair instrument as described in claim 7 wherein, near said first end having said wing device, there is a rim-type flange extending about a part of the circumference of said cylindrical member outward therefrom at least 0.5 cm.

10. A rectovaginal surgical repair instrument comprising:

(a) a smooth, rigid elongated cylindrical member having a first end and a second end, said cylindrical member having a length in the range of 3 cm to 15 cm and a diameter such that at a widest point of said cylindrical member said diameter is in the range of 1 cm to 4 cm; and (b) at least one rigid pinch-type clip rigidly attached to and extending outwardly from, said first end.

11. A rectovaginal surgical repair instrument as described in claim 10 wherein said cylindrical member has a continuously curved shape at said second end.

* * * * *